United States Patent
Lai

(10) Patent No.: US 8,409,177 B1
(45) Date of Patent: Apr. 2, 2013

(54) INTRASTROMAL REFRACTIVE SURGERY BY INDUCING SHAPE CHANGE OF THE CORNEA

(76) Inventor: Shui T. Lai, Encinitas, CA (US)

( * ) Notice: Subject to any disclaimer, the term of this patent is extended or adjusted under 35 U.S.C. 154(b) by 1687 days.

(21) Appl. No.: 11/549,398

(22) Filed: Oct. 13, 2006

Related U.S. Application Data

(60) Provisional application No. 60/726,424, filed on Oct. 13, 2005.

(51) Int. Cl.
*A61B 18/20* (2006.01)

(52) U.S. Cl. .................... 606/4; 606/5

(58) Field of Classification Search .......... 606/2–19
See application file for complete search history.

(56) References Cited

U.S. PATENT DOCUMENTS

| | | | | |
|---|---|---|---|---|
| 5,196,027 A | * | 3/1993 | Thompson et al. | 128/898 |
| 5,201,763 A | * | 4/1993 | Brady et al. | 623/6.11 |
| 5,549,632 A | | 8/1996 | Lai | |
| 5,722,971 A | * | 3/1998 | Peyman | 128/898 |
| 5,825,562 A | | 10/1998 | Lai et al. | |
| 5,984,916 A | | 11/1999 | Lai | |
| 6,171,336 B1 | | 1/2001 | Sawusch | |
| 6,210,401 B1 | | 4/2001 | Lai | |
| 6,325,792 B1 | * | 12/2001 | Swinger et al. | 606/4 |
| 6,450,642 B1 | | 9/2002 | Jethmalani et al. | |
| 6,706,036 B2 | | 3/2004 | Lai | |
| 6,761,454 B2 | | 7/2004 | Lai et al. | |
| 6,813,082 B2 | | 11/2004 | Bruns | |
| 6,836,371 B2 | | 12/2004 | Lai et al. | |
| 6,934,088 B2 | | 8/2005 | Lai et al. | |
| 6,976,641 B2 | | 12/2005 | Lai et al. | |
| 2001/0027314 A1 | | 10/2001 | Peyman | |
| 2003/0003295 A1 | | 1/2003 | Dreher et al. | |
| 2003/0013339 A1 | | 1/2003 | Pan | |
| 2003/0143391 A1 | | 7/2003 | Lai | |
| 2004/0243112 A1 | | 12/2004 | Bendett et al. | |

FOREIGN PATENT DOCUMENTS

| | | |
|---|---|---|
| WO | 96/06883 A1 | 3/1996 |
| WO | 02/076320 A1 | 10/2002 |
| WO | WO 2005/038015 A1 | 4/2005 |
| WO | WO 2005/062818 A2 | 7/2005 |
| WO | WO 2007/044967 A2 | 4/2007 |
| WO | 2007/044967 A3 | 9/2007 |

OTHER PUBLICATIONS

PCT Notification of Transmittal of the International Search Report and the Written Opinion of the International Searching Authority, or the Declaration, dated Jul. 26, 2007.
PCT Notification Concerning Transmittal of International Preliminary Report on Patentability (Chapter I of the Patent Cooperation Treaty) in PCT Application No. PCT/US2006/040393, dated Apr. 24, 2008, 8 pages.
Supplementary Partial European Search Report, for European patent application 06826038.9, dated Nov. 2, 2009, 9 pages.

* cited by examiner

*Primary Examiner* — Aaron Roane
(74) *Attorney, Agent, or Firm* — SF Bay Area Patents, LLC; Andrew V. Smith

(57) ABSTRACT

A shape change is induced in a cornea for treating a keratoconus condition, and/or correcting a refractive error and/or a high order aberration. A beam of laser pulses is focused to a stromal layer of a patient's eye, and an intrastromal pocket is ablated. An injection port is cut between the intrastromal pocket and a cornea surface of the eye. A polymerizable fluid is flowed into the intrastromal pocket through the injection port. The fluid is cured to form a polymeric insert, and thereby inducing a cornea shape change.

37 Claims, 5 Drawing Sheets

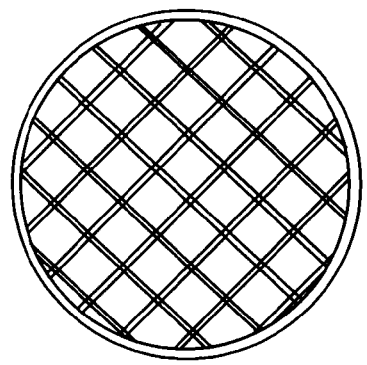
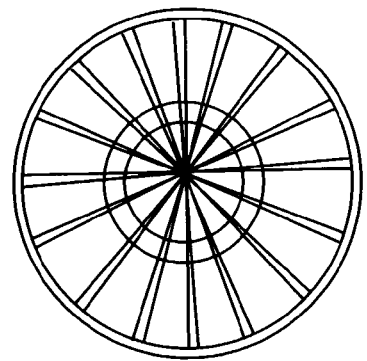
Fig. 2A    Fig. 2B
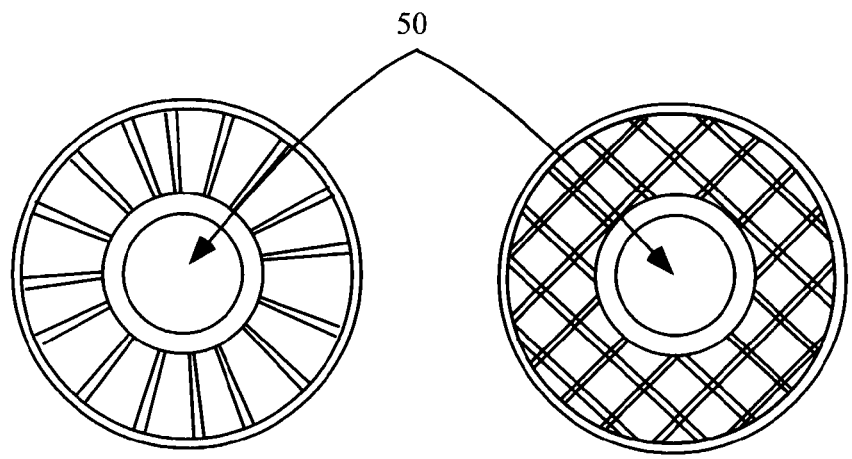
Fig. 2C    Fig. 2D

INTRASTROMAL REFRACTIVE SURGERY BY INDUCING SHAPE CHANGE OF THE CORNEA

PRIORITY

This application claims the benefit of priority to U.S. provisional patent application No. 60/726,424, filed Oct. 13, 2005, which is hereby incorporated by reference.

BACKGROUND

1. Field of the Invention

The invention relates to inducing a shape change in a cornea for treating a keratoconus condition, or correcting a refractive error or a high order aberration, or combinations thereof, and particularly to generating an intrastromal pocket within a patient's eye and filling with a polymeric insert.

2. Description of the Related Art

Keratoconus is an eye condition that involves bulging of the cornea usually associated with local thinning of the cornea. It is difficult to treat. Most treatments provide temporary solutions that do not result in high quality vision. Hard contact lenses or Rigid Gas Permeable (RGP) lenses may be used to "cover" over the cone of the eye. However, this can result in high distortion and does not achieve optimal vision. Rubbing of the lens on the cone often leads to thinning of the cornea, cornea melt, or other worsening conditions. Laser ablation may be tried for shaving off a protrusion. This cuts against the common sense notion that further thinning would likely lead to worsening conditions. "Intacs", which are thin strips of plastic (PMMA), may be inserted inside the cornea to attain a less distorted eye. By trial and error, the method may have occasional success, but is unlikely to produce reliable results. It is desired to have a method of corneal surgery that can treat Keratoconus and/or can restore a quality of vision that existed prior to the onset of the Keratoconus condition.

With the advent of wavefront technology, one can now measure minute amounts of ocular aberrations. In fact, none of the current refractive surgery methods, such as Laser In situ Keratomileusis (LASIK), Laser Epitheial Keratomileusis (LASEK), Conductive Kerotoplasty (CK), or Refractive lens exchange, have the ability to modify the eye to achieve the level of accuracy of that of a wavefront aberrometer. Some underlying issues with current refractive surgeries include inaccuracies in surgical methods that induce more optical distortions than they reduce, and traumatic aspects of procedures that induce aggressive healing that negates intended results of the surgery, and can cause vision instability during a healing period.

Currently, the most practiced refractive surgery is LASIK, which involves the creation of a flap, a thin layer of cornea tissue excised by a microkeratome. That procedure often introduces complications such as buttonhole, loss of flap, incomplete flap, and/or epithelium cell ingrowths. The cornea is structurally weakened by LASIK, and cases of estasia have been found in many LASIK patients. Hence, it is desired to provide a refractive surgery method that is safer than LASIK, is less traumatic, provides quicker vision recovery, and/or is reversible.

Techniques of customized ocular aberration correction that cancel aberrations of an individual eye by incorporating wavefront correction in a spectacle lens are described in US patent applications 20030003295A1, 20030143391A1, and 20030143391A1, and in U.S. Pat. No. 6,813,082, which are hereby incorporated by reference. However, these involve careful alignment of the spatial profile of wavefront correction on the eyeglasses with that of the eye in order to achieve maximum benefit. Eyes tend to move at various glaze angles, resulting in a limited usefulness if a maximal cancellation of wavefront aberrations is desired at all times, including when the eye moves to the various glaze angles.

Recently, Advanced Medical Optics introduced Technis, which is an intraocular lens that incorporates a fixed amount of spherical aberration correction. However, the same amount of correction does not provide optimal correction for every eye. Because it is not customized for each patient, the benefit may therefore be limited.

SUMMARY OF THE INVENTION

A method is provided for inducing a shape change in a cornea for treating a keratoconus condition, or correcting a refractive error or a high order aberration, or combinations thereof. A beam of laser pulses is generated. The beam is focused to a stromal layer of the patient's eye. An intrastromal pocket and an injection port are ablated within the patient's eye. The injection port is between the intrastromal pocket and a cornea surface of the eye. A polymerizable fluid is flowed into the intrastromal pocket through the injection port. The fluid is cured to form a polymeric insert, thereby inducing a cornea shape change.

A pocket location is preferably selected near a cornea center or offset from a cornea center toward a cone.

The laser may be a femtosecond surgical laser. A cut pattern may include multiple linear cuts.

An applanator is preferably applied to the cornea surface for conforming the eye according to an applanator surface curvature. A transition zone may provide a gradual radius of curvature change from an optical zone to an outer zone. The curing preferably includes applying UV light through a mask to provide a pattern for the polymeric insert. The polymeric insert may have an approximately 5-150 micron thickness, or approximately 10-75 micron thickness.

The injection port is preferably sealed. One or more further injection ports may be cut between the intrastromal pocket and the cornea surface of the eye. Polymerizable fluid may be flowed into the intrastromal pocket through the one or more further injection ports.

A second intrastromal pocket may be ablated within the patient's eye. Polymerizable fluid may be flowed into the second intrastromal pocket through the same or a different injection port.

The polymerizable fluid may be pre-mixed with one or more non-toxic light absorbing agents. A bleachable absorbing agent may be added to the polymerizable fluid.

The polymeric insert may have regions of different selected thicknesses for correcting wavefront aberration.

The curing preferably includes photoreactive curing with curing light. Thermal curing may also be applied.

A method of changing the shape of a cornea is also provided. A substantially closed pocket is generated in a stroma of an eye. At least one opening connects a cornea surface to the pocket. The size of the opening is substantially smaller than an area of the pocket. A polymerizable fluid is injected in the pocket through the opening. An anterior surface of the cornea is in contact with a shaped surface of an applanator. Radiation energy is applied to cure the injected material for forming a rigid layer, and to maintain a permanent shape change of the cornea. The shaped surface of the applanator may conform the cornea and decrease a diopter value, radius of curvature or an assymmetry of the cornea to correct a myopia, hyperopia or astigmatism condition of the eye, or correct a wavefront aberration, or combinations thereof.

The shaped surface of the applanator may conform the cornea to reduce a bulge of a cone to correct a keratoconus condition of the eye. The rigid layer may have an optical zone that corrects a refractive error of the eye, and a transition zone that changes a radius of curvature from that at an inner edge of the transition zone to that of a base cornea curvature at an outer edge of the transition zone. A cured pattern of injected fluid may form a plurality of openings in the form of grids across the rigid layer. The method may be reversible including removing the material of the rigid layer using a scissor and cutting the material through a small opening at the cornea.

The polymer fluid may be cured to provide an optical path difference (OPD) map for substantially canceling a wavefront aberration of the eye. The OPD map may be substantially built by a thickness profile of cured material, a change of index of refraction in injected polymer, or a volume expansion of cured material in the rigid layer.

The polymerizable fluid may include a light activated component and a thermally activated component, such that the light activated component provides the rigid layer, and the thermally activated component increases a viscosity, or turns into solid, or a combination thereof, of remaining uncured material.

A method of enhancing a mechanical strength of a cornea is also provided. A pocket is generated in a stroma of an eye having an opening to a cornea surface substantially smaller than a size of the pocket. A polymerizable fluid is injected into the pocket through the opening. Radiation energy is applied to the injected fluid to form a rigid layer. Thermal curing may also be applied to the rigid layer or injected fluid or both.

A curable polymerizable fluid for forming a rigid material of predetermined thickness within an intrastromal layer of an eye is also provided. The polymerizable fluid includes a mixture of monomeric and polymeric sub-components. An activation agent absorbs a radiation source and causes the monomeric and polymeric subcomponents of the mixture to cross-link to form a cured layer. A bleachable agent absorbs substantially an activation radiation in a shallow layer. The bleachable agent has an absorption coefficient that is small compared to an overall thickness of the cured layer and of an order of accuracy of an intended thickness of a layer of cured polymer. The polymeric layer may be approximately 5-150 microns in thickness, or approximately 10-75 microns in thickness.

A method is also provided for curing an intrastromal layer of polymer to an intended thickness. A polymer mixture of monomers, polymers and an activator that causes cross-linking are provided into a prepared intrastromal pocket. A broad area activating radiation source is provided. A bleachable agent concentration and radiation source intensity are selected such that the bleachable agent absorbs substantially the activating radiation in a shallow layer and bleaches with a bleach time T, and wherein the bleachable agent has an absorption coefficient that is small compared to an overall thickness of the cured layer, and of an order of accuracy of an intended thickness of a layer of cured polymer. The polymer mixture is irradiated for a time period of approximately N times the bleach time T, wherein N comprises approximately an intended thickness divided by said absorption coefficient of the bleachable agent. The polymeric insert may be approximately 5-150 microns in thickness, or approximately 10-75 microns in thickness. The polymer mixture may also be thermally cured.

A further method of changing a shape of a cornea is provided. Multiple excision channels are formed in the stromal layer of a cornea as well as at least one opening connecting a cornea surface to the channels. A size of each opening is substantially smaller than an area occupied by the channels. A polymerizable fluid is filled into the channels through the at least one opening. An anterior surface of the cornea is conformed to a shaped surface of an applanator. Radiation energy is applied to the fluid to form a rigid layer for maintaining a permanent shape change of the cornea.

The channels may form a grid-like configuration or a spoke-like configuration, or a combination thereof. The channels may include multiple spokes. There may be one or more rings among the channels approximately normal to the spokes. The spokes may terminate at a predetermined radius from a center, thereby leaving a central portion of predetermined radius devoid of channels, or the channels may terminate at a center point.

An applanating device is provided for changing a shape of a cornea of an eye. An applanator has one surface for viewing and a shaped surface that provides a changed shape of the cornea. A closed pocket is defined within a stroma of a cornea and has a substantially intact tissue connection between an anterior stromal layer at the pocket and a remainder of the cornea. An opening defined on the cornea has a size substantially smaller than an area of the pocket. A channel is defined within the cornea connecting the opening to the stromal pocket. A pathway is thereby provided for injecting a polymerizable mixture into the stromal pocket that is curable by activating a curing of the polymerizable mixture with a light source to form a rigid layer of polymerized material of selected shape and size. Alignment marks may be provided for aligning the shaped surface to an entrance pupil of the eye.

Combinations of any of the features and/or techniques provided above or below herein are also provided with great advantage.

BRIEF DESCRIPTION OF THE DRAWINGS

FIG. 2a schematically illustrates a grid pattern of a cured intrastromal layer in accordance with an embodiment.

FIG. 2b schematically illustrates channels having a spoke pattern of a cured intrastromal polymeric layer in accordance with an embodiment.

FIG. 2c schematically illustrates channels having a spoke pattern of a cured intrastromal layer having a central region devoid of channels in accordance with an embodiment.

FIG. 2d schematically illustrates channels having a grid pattern of a cured intrastromal layer having a central region devoid of channels in accordance with an embodiment.

DETAILED DESCRIPTION OF THE PREFERRED EMBODIMENTS

A technique is provided for inducing a shape change of a cornea, particularly in the region of a cone or a bulging in Keratoconus eyes.

A further technique is provided for changing a curvature of an anterior surface of the cornea to cause a correction of a refractive error, such as myopia, hyperopia and/or astigmatism.

Another technique is provided for wavefront correction of a high order aberration of an eye. The high order may be defined as a third or higher order Zernike polynomial of the aberration.

Curing light and UV light are generally used interchangeably in the description that follows, with the understanding that curing light may have other wavelengths than UV. That is, curing light may include part or all of the UV spectrum, and may include wavelengths other than UV that are suitable for curing particular materials.

Low Trauma Surgery Using an Intrastromal Pocket

An intrastromal pocket is created in the stromal layer of the eye. An intrastromal pocket is a region inside the cornea where stroma collagen is separated, and in this space a proprietary material may be injected to achieve a cornea shape change.

The location of the pocket is preferably near the center of the cornea, but in the case of treating keratoconus, the pocket may be offset towards the location of the cone, and preferably include the area of the cone. An intrastromal pocket may be created by making an incision with a depth-calibrated knife, such as Radial Keratotomy (RK) knives. The depth of the cut is therefore well controlled. A pocket at a predetermined depth of about 100 to 400 microns may then be made using a scalpel and/or blunt specula at the incision depth and separates the stromal layer. Alternatively, to make a highly precise excision, a femtosecond surgical laser such as those manufactured by IntraLase, Irvine, Calif., may be used to make a highly precise tissue cut at a predetermined location, with specific pocket size and at desired depth. A description of a preferred laser device, and method of its uses, particularly for the eye, have been provided in U.S. Pat. Nos. 5,549,632, 5,984,916, and 6,325,792, which are hereby incorporated by reference. To make a pocket with a femtosecond laser, the laser beam is directed inside the stromal layer, with its focal ablation spot at the location and depth as specified by the surgeon. A planar cut of desired diameter ranging from 2 to 9.5 mm is then made. A planar cut refers to an intrastromal excison that is substantially in a "plane" parallel to the cornea surface. An example of a planar cut is illustrated in FIG. 1a.

Figure 1A:
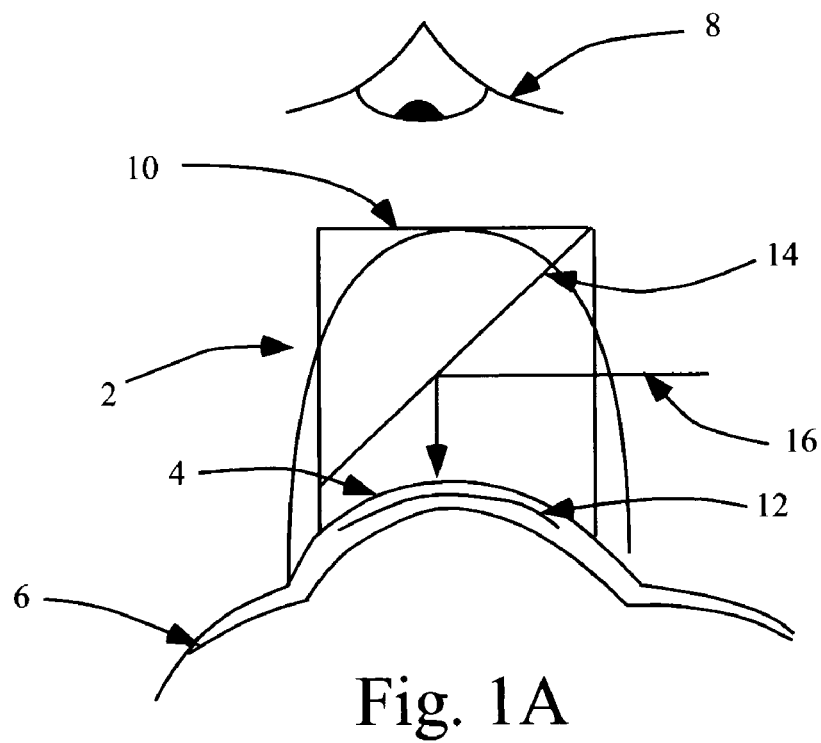
FIG. 1a schematically illustrates an applanating device for conforming a cornea shape.

FIG. 1a generally shows an applanator 2 having a shaped contact surface 4 in contact with a patient's eye 6. A surgeon's viewing 8 is shown above a flat surface 10 opposite the contact surface 4. An intrastormal pocket 12 is shown after having been cut preferably by a femtosecond laser. The applanator 2 of FIG. 1a includes a UV reflector 14 which permit curing light 16, which is preferably UV light but may have any wavelength sufficient to cure the polymeric material inserted into the pocket 12, to be incident transversely to the applanator 2 allowing the surgeon to view 8 directly into the eye 6.

To make a pocket with a femtosecond laser, the cut pattern preferably includes a plurality of linear cuts, which may be made by a pulsed laser operating at a repetition rate in a range from 1000 Hz, or multiple thereof, to several hundred thousand Hz, and may be 10,000 Hz or multiples thereof, 50,000 Hz or multiples thereof, or 100,000 Hz or multiples thereof, 150,000 Hz, 200,000 Hz, or 300,000 Hz. Each subsequent line is to be positioned next to the previous line. The width of the tissue line cut by the laser is defined as the width of the line resulting from tissue ablation. This width is a function of focal spot size, and the amount of laser energy deposited in each laser pulse while the line cut is made. To achieve a pocket, namely a clean separation of tissue, each laser line cut is overlapped with the line width of the previous cut line. The range of overlap is preferably from about 30% to 70%, and may be 40%, 50% or 60%, for example. When the overlapping lines have formed a circular patch or other shape for the pocket, a planar pocket is deemed to have been made.

Alternatively, the planar cut can be made with spiral or circular lines. In this case, a spiral can start from the center of an intended planar pocket position, and spiral outwards. Each ring may have a similarly prescribed overlap with a previous ring tissue line width as described earlier in the case of a linear cut pattern, to achieve a clean tissue separation in the pocket.

Figure 3:
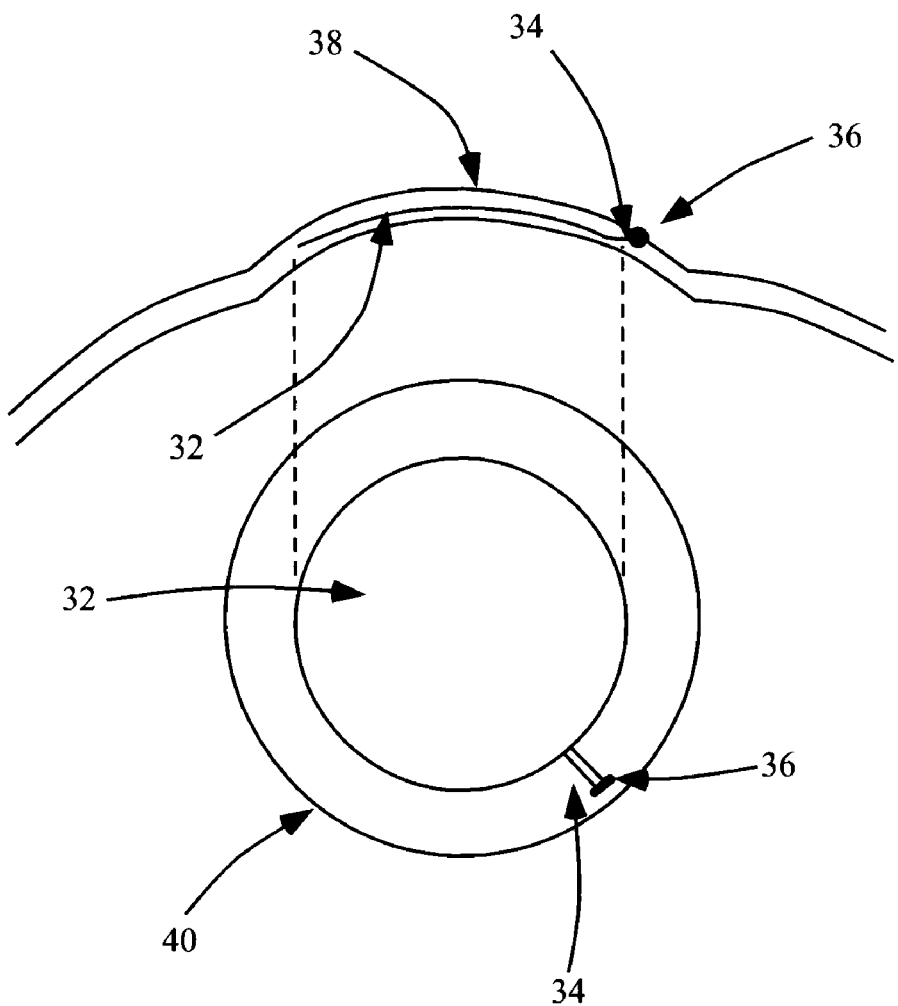
FIG. 3 schematically illustrates an eye treatment in accordance with a preferred embodiment including injecting a polymerizable fluid through an opening to an intrastromal pocket in accordance with a preferred embodiment.

After a planar pocket is made, the femtosecond laser is preferably used to cut an opening for the material injection port. This injection port can be a channel that connects the planar pocket to the outer surface of the cornea. For a pocket size substantially smaller than 6 mm in diameter, the channel may have a part that extends towards the limbus at a point 4 to 5 mm from the center of the cornea, then the channel connects to the surface of the cornea as illustrated at FIG. 3. By having an injection opening far from the optical center, the distortion caused by insertion of a cannula and material is minimized. As used herein, the term "pocket" is not meant to include the space under a conventionally-separated LASIK flap. The pocket here is preferably a "closed pocket", wherein the connection to the outside of the cornea is through the material injection port, which is preferably small in size, of about 1-3 mm in a preferred embodiment. A feature of the pocket is that the anterior portion of the cornea pocket is held intact to the eye, as compared to a LASIK flap that is separated from the rest of the cornea.

In a LASIK flap, the flap layer of cornea has lost the connection with its surrounding tissue, and it no longer contributes any tensile strength to hold the intraocular pressure of the globe. The mechanical structure of the cornea as a whole is weakened, and the globe may be now held by a thinner stromal layer of 300 microns or less of stromal tissue, versus 500 microns or more tissue in a normal cornea.

In an embodiment, the femtosecond laser is used to vaporize a precise tissue volume, rather than making a planar cut. The volume can include a uniform thickness layer of 10 to 150 microns, with a diameter ranging from 2 mm to 9.5 mm. Alternatively, the layer can take the shape of a lenticule, a thin lens with either a positive or a negative refractive power, and the lenticule diameter may range from 2 mm to 9.5 mm. This pocket is filled with biocompatible material and the stromal layer anterior to the pocket is connected intact to the eye. It actually provides a strengthening effect to the eye, especially in keratoconus eyes. It prevents estasia, and in the case of keratoconus or LASIK eye, it can reverse estasia.

A procedure in accordance with a preferred embodiment is generally less invasive than PRK, LASIK, LASEK, CK, and/or Refractive Lens Exchange procedures. In a preferred method, the Baseman Membrane at the epithelium is preserved. This reduces the hyperplasia that causes haze following an aggressive healing after Photorefractive Kerotoplasty (PRK) and LASEK. The epithelium remains intact; which results in less pain, and a quicker visual recovery. The procedure does not involve the making of a LASIK flap, since the separated stroma in a stromal pocket does not form a "flap". Therefore, no slipping, sliding, nor a free flap results from a procedure in accordance with the preferred embodiment.

Polymerizable Fluid

Once the pocket is made, a polymer fluid can be then introduced inside the stromal pocket. The fluid can be introduced using a syringe with a straight or angled cannula tip. Other methods of injecting the fluid can also be used. The objective is to introduce the fluid inside the cornea at a predetermined location, and the material to be spread over a predetermined area, and at a predetermined depth inside the stroma, as determined by the size and location of the pocket.

The polymer fluid is chosen for its biocompatibility, and preferably remains stable inside the cornea. The polymer includes monomers, polymers, and/or photo or thermally activated agents, and preferably all of these. Under the excitation of curing radiation or a curing energy source (activation source), they form cross-links among themselves, or other polymer components to form a polymer network. Preferably, the network is biocompatible with the cornea collagen. In one embodiment, a cross-linked polymer forms a rigid structure. The network is preferably porous to allow oxygen and nutrients to pass through with minimum blockage. The network is formed inside the corneal pocket and around the collagen fibers anterior and posterior to the pocket, forming a mechanically stable layer structure, which can be in the shape of a thin layer, or a lenticule. One benefit of such structure is to provide stability and re-enforcement to the Keratoconus region where the cornea is thinner.

Examples of the polymer fluid can be chosen from a list of photo and thermally activated polymer systems. The polymer fluid may include without limitation, Siloxane polymers, acrylates, such as MMA, PMMA, cellulosic polymers, carbonates, silicone acrylates, fluoroacrylates, perfluorinated polyethers, allyl substituted acetylenes, HEMA (2-hydroxyethymethacrylates), fluoropolymers, thio or ene systems, epoxies, isocyanates, fibrinogen, or other known types of Rigid Gas Permeable (RGP) or soft contact lens material, preferably with good DK value or porosity, synthetic cornea materials such as Alphcor, or hydrogel based material, mixtures, or combinations of any of the above, and modifications in its chemical or structural forms and additives for the purpose of enhancement of: its rigidity, oxygen permeability, or nutrient passage properties, or combinations thereof. Generally speaking, any polymers with desired characteristics can be used.

Changing the Shape of the Cornea

Once the polymer fluid is introduced inside the pocket, time is provided for the polymer to disperse, to form a somewhat uniform planar layer or a lenticule in the pocket. In one embodiment, upon the material spreading being completed, an applanator device is applied, and put into contact with the cornea, to make the eye conform to the curvature of the applanator surface. The applanator also serves as an eye stabilizer, to minimize inaccuracy or errors due to eye movement when the treatment procedure is being performed. A method of using an applanator for the stabilization of the eye movement and for precisely delivering laser pulses in the cornea is described in U.S. Pat. No. 5,549,632, which is incorporated by reference.

In the case of treating a Keratoconus condition, the present method reduces or totally eliminates the bulging of the cone. Before treatment, the biometry of the eye is measured, such as the axial length, cornea curvature, and refractive errors which can be measured in terms of second order Zernike polynomials namely, wherein the sphere and astigmatism which are typically determined in a manifested refraction, using an auto-refractor, corneal topography or a wavefront aberrometer. Based on the shape of the cornea and its axial length, the keratoconus cone and the refractive errors can be mathematically subtracted, resulting in a non-keratoconus corneal surface. This ideal surface should ideally provide an unaided vision 20/20 or better. In a non-keratoconus eye, the ideal surface shape is one that the sphere and astigmatism errors are removed or subtracted out. Furthermore, an aspherical component such as the Zernike Z(4,0) term, can be included to form a prolate shaped cornea as an improvement.

Now, this surface shape of a repaired eye can be milled by CNC machine to form the contact surface 4 of the applanator 2 illustrated at FIG. 1*a*. Alternatively, the shaped contact surface 4 of the applanator 2 can also be formed by molding methods. By applanating this CNC surface 4 to the eye 6, the surface curvature of the applanator 2 conforms the cornea surface. In one embodiment, the radiation source for curing the injected material can be a curing light 16 comprising UV or other wavelengths. It may also comprise an electrical or magnetic energy source that can cure the material. The applanator 2 is made of material transmitting the curing light 16, preferably UV transmitting. It may have a flat surface 10 on the other end of the applanator 2 where the curing light 16 passes the applanator 2, enters the cornea and interacts with the polymer to form a cross-linked structural framework as discussed above. Once the material is cured, the cured material forms a rigid layer. The outer surface of the cornea is fixed to that of the contact surface 4 of the applanator 2. The applanator 2 is then removed and a permanent and refractive error-corrected anterior cornea shape is formed.

Figure 1B:
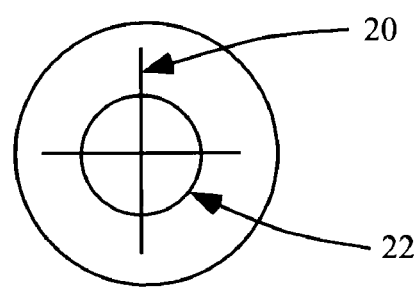
FIG. 1b schematically illustrates an alignment tool of the appanating device.

The applanator 2 may have many forms, and so some examples follow for illustrating relevant features: As illustrated at FIG. 1*b*, cross-hairs 20 and at least one alignment ring 22 between 2 and 6 mm in diameter, e.g., 3 mm, 4 mm or 5 mm, are preferably inscribed in the applanator 2 for alignment with the entrance pupil and the visual axis. In another embodiment, a 45 degree reflector 14 may be incorporated to direct curing light, which can be a UV light source, at approximately 90 degrees from the line of sight 8 of the surgeon. An entrance port is provided for a fiber optic cable. In this example, the surgeon can see through the applanator 2 and the cornea while curing light 16 is applied. The angle of the turning reflector 14 may vary, as may the spectral contents of the light source, as long as the configuration delivers curing energy to the polymer material. In this example, the surgeon has an unobstructed view 8 of the patient's cornea while the curing light 16 is applied. A foot-switch can be connected to the light source and its power supply unit for turning the light on and off. One may further incorporate a light intensity monitor, a light dosage accumulator and/or an automatic timer to turn off the light source when the curing is completed, to accomplish controlled and repeatable results.

Generating Spatial Patterns in the Cured Material

A curing light intensity profile can be controlled by a mask with a specially designed spatial attenuation profile (a two dimensional spatial attenuating density filter) (see U.S. Pat. No. 6,813,082 by Bruns, which is hereby incorporated by reference). If the light source has a uniform intensity in the X-Y dimension, the light intensity after passing through such mask would have a spatial intensity that corresponds to the transmission profile of the mask. Therefore, the spatial beam profile may be controlled by the spatial attenuation of the incident beam. A scanning method in combination with a tightly focused beam spot may be used for a tight spatial confine of the curing action, at a tight focal point of the beam waist (see US application 2003/0143391A1 by Lai, which is assigned to the same assignee as the present application and is hereby incorporated by reference). In this case, curing is controlled by the dosage of photon energy at the focal spot.

Using a laser light delivery method such as those described in U.S. Pat. No. 6,813,082 or US 2003013339A1, one may cure the polymer at a location in the corneal pocket, with a desired dosage, and be able to create many of the curing patterns described in the following.

The Forms and Shapes of the Cured Layer

Several innovative designs of the cured layer in the corneal pocket are illustrated here. Other shapes or forms may be based on these designs, e.g., with minor dimensional or pattern modifications that can be adapted in alternative embodiments.

Thickness of the Cured Layer

The cured layer is preferably thin, to minimize an obstruction by water, oxygen, and/or one or more nutrients passing through the layer. The cured layer is preferably porous in its polymer network structure to facilitate nutrient transport. The range of the layer thickness is between about 2 microns to 150 microns, preferably in the range of 10-75 microns, e.g., including multiples of 2, 3, 5 and 10 microns.

Pattern Structure of the Cured Layer

To further enhance nutrient transport, a method may include providing a "grid pattern" structure, such that a portion of the layer is totally un-obstructed to nutrient pass-through. Examples of such pattern are illustrated at FIGS. 2(a)-(d).

A straight-line grid, with a ring border is illustrated in FIG. 2(a). A radial grid pattern with one of more concentric reinforcement rings is illustrated in FIG. 2(b). In FIG. 2(c), a central (optical zone) region of the layer is clear and open, and in (d) the central region is solidly filled with cured material. In FIG. 2(c) or 2(d), the grid pattern can include radial lines and/or crosshatch, as illustrated. Another embodiment includes a porous structure of "grids", with the openings being preferably irregular in shape and arrangement. The blocked and opening regions are preferably randomized in their locations. A computer program may generate a curing light mask by randomizing locations, and transmission/blocking of the location in the light mask. One advantage of such a randomized pattern is to eliminate a possible diffraction effect, which could result from having a regular grating structure of grids.

Channel Structure of Intrastromal Pocket

In a further embodiment, individual channels are excised by a femtosecond laser. One such example is illustrated at FIG. 2(c). Instead of being a cured pattern of injected material as previously described, FIG. 2(c) now represents a laser excison channel pattern. A femtosecond laser is applied to cut out intrastromal channels. Injected material is then filled in these channels, and the applanator 2 is applied to conform the shape of the cornea. Then, cured material in the channels holds the changed shape of the cornea. One advantage here is that the stroma outside of the channels has not been separated. Less trauma and a quicker vision recovery are further advantages. The cornea thickness will conform to the applanator as previously described and a permanent shape change is achieved after curing. In this case, the posterior stroma of the pocket is unlikely to separate from the anterior stroma in the pocket. The injection of material may involve multiple injection ports to facilitate the filling and spreading of the material in all the channels.

FIG. 3 schematically illustrates an eye treatment in accordance with a preferred embodiment. A stromal pocket 32 is shown in side and top views. The stromal pocket 32 is shown fluidly communicating with a channel 34 having an opening 36 at a cornea surface. A polymerizable fluid is injected through the opening 36 and along the channel 34 to the intrastromal pocket 32 in accordance with a preferred embodiment.

The Reversibility of the Procedure

Another advantage of a technique in accordance with a preferred embodiment in comparison to typical LASIK, PRK, or CK, is its reversibility. For any reason, if it is desired that the procedure be reversed, a small incision, e.g., 1-2 mm, preferably near the limbus 40, can be made to reach the cured material. A small angled scissor may be inserted to cut the cured material into smaller pieces. Each small piece may then be pulled out; e.g., one at a time, until the cured injected material is removed.

Sealing and Reopening of the Material Injection Ports

If desired, the injection port(s) can be sealed by stitches or tissue glue such as Fibrin glue, which can be activated with thrombin. Tissue glue is commercially available as Tisseel, from Baxter International, Deerfield, Ill. In another embodiment, after injection of material, the injection opening may be sealed. Applanation and curing is then performed. At or near the end of the curing period, the injection ports can be re-opened by an incision for drainage of excessive material and/or to minimize unused material in the cornea pocket.

Controlling the Thickness in Cured Material by Controlling the Absorption Characteristics of an Additive Another advantageous embodiment provides control thickness of the cured material. This may be accomplished by controlling the curing light penetration and/or its attenuation depth, and the rate or degree to which the light-absorbing agent is consumed during the curing process. For a given wavelength in the curing light, one can pre-mix in the injected material one or more light absorbing agents that is/are non-toxic to the eye and is/are readily absorbed and disposed of systematically if not used in the curing. In one embodiment, for example, one mixes in the injected material absorbing agents that would contribute a high percentage say, 95% of the curing light, and an appropriate amount of photo-activators to absorb 5% of the curing light.

The absorbing agents are chosen such that they are bleached under the curing light irradiation. For example, if one intends to have a cured material layer thickness of 20 microns, one can design a mixture of the absorbing agent and the activator such that the light attenuation of the entire material mixture has an absorption depth of about 5 microns or less. Furthermore, the exposure time and the light intensity of the curing light source are also controlled such that the absorbing agent in the first 5 micron layer is consumed or bleached after an exposure period of, for example, 10 seconds. After 10 seconds, the absorbing agents in the first 5 microns of the material are substantially fully bleached and at the same time the photo-activators have fully cured the material in the first 5 microns of the material. The curing light intensity is now almost at its full intensity, because it transmits through the first 5 micron layer basically without attenuation due to lack of absorbing agent. Therefore, in another 10 seconds, the photo-activators in the second layer of 5 microns are activated and the material cured, and so on. Therefore, in about 20 seconds, one can cure a material layer of about 10 microns. If one also includes light leakage during the first 10 seconds, it will take less than 20 seconds to substantially totally bleach the absorbing agents in the second 5 microns.

Figure 4:
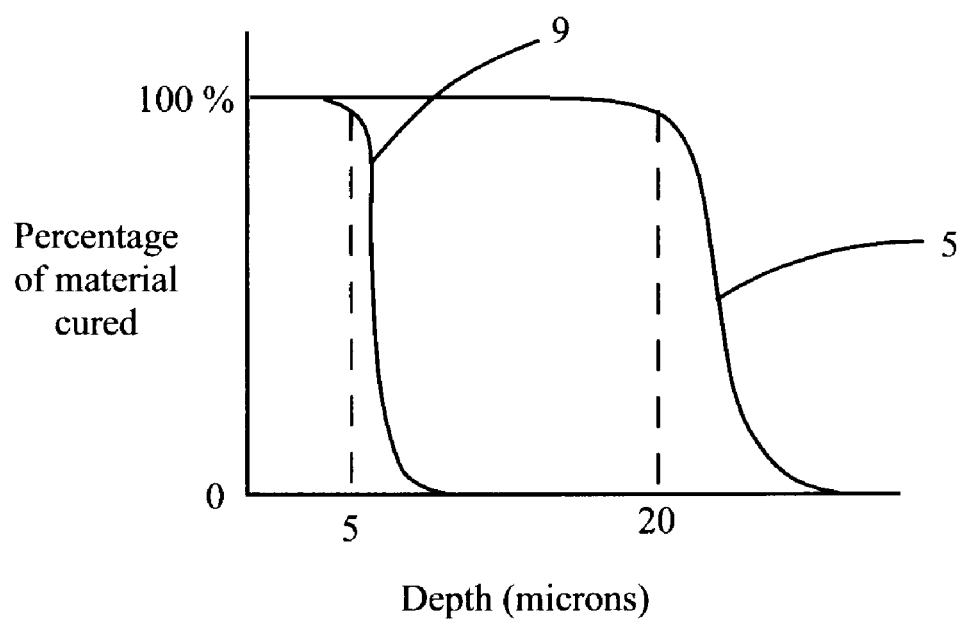
FIG. 4 shows plots of curing material percentage versus depth of curing.

A graphic representation of the extent of the material cured versus time is illustrated in FIG. 4. Plots 9 and 5 illustrate the percentage of the material cured versus depth in the first 10 seconds and after 40 seconds, respectively, of curing exposure using parameters given in the present example. By controlling the attenuation depth and the bleachable characteristics of the absorbing agent, one can control a cured thickness of the polymer layer. In one embodiment, an additive absorbing agent is also a photo-activator.

The absorbing agent and the photo-activator in the deeper part of the injected polymer, which may not have been cured, can also act as a UV blocker to prevent unsafe exposure of the UV to the retina. Alternatively, one may also add a UV blocking ingredient in the injected material.

Examples of Refractive Surgery Procedures
Treatment of Myopia and Hyperopia

The diopter power of the cornea (which is inversely proportional to radius of curvature of the cornea), is reduced in a myopia treatment. The cornea is pushed down to flatten it to a desired degree. Likewise, for a Hyperopia treatment, the diopter power value is increased. The curvature of the applanator contact surface is constructed accordingly to decrease the cornea curvature. For a hyperopia treatment, one embodiment is to provide at least one air vent near the central region where the cornea apex is. This allows trapped air to vent out while applanating the cornea. The vent or vents can also be used to generate a vacuum for a better attachment of the cornea to the applanator. In eyes with astigmatism, the lack of symmetry indicates a degree of astigmatism in the cornea. To correct an astigmatic eye, the applanator surface may be shaped to be rotationally symmetric or to remove asymmetry thereof.

Transition Zone

In one embodiment, a more uniform stress distribution is provided on the cured material layer. An analysis of the mechanical stress as a result of such curvature change in the cornea indicates that a zone with increased stress is around the transition region, where the change of curvature occurs. To avoid excessive localized stress, one embodiment provides a radius of curvature transition zone, a region where the curvature is changing gradually from the treated central optical zone curvature to the baseline eye curvature at 9-10 mm diameter.

Figure 5:
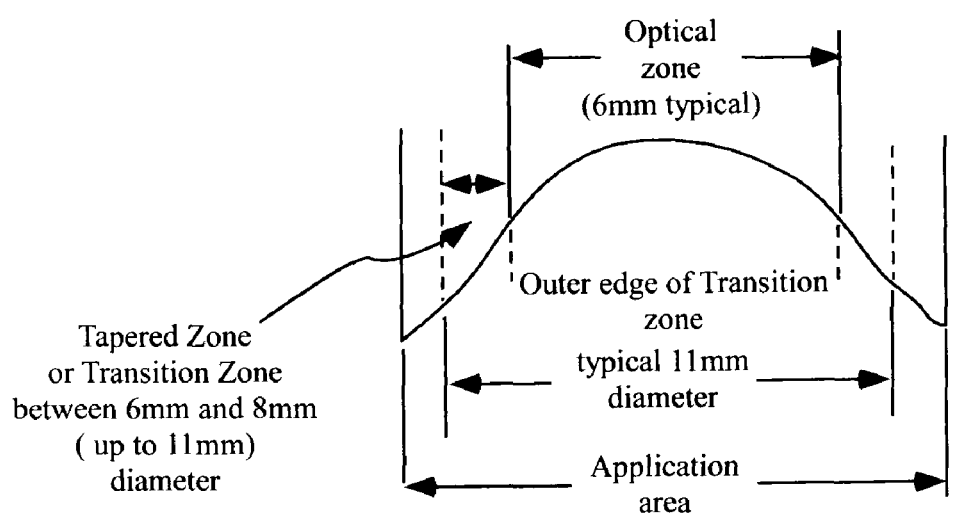
FIG. 5 illustrates a transition zone within an applanation area in accordance with a preferred embodiment.

FIG. 5 illustrates an optical zone and a transition zone, and base of the cornea at the limbus. A range of the optical zone is 2 mm to 6.5 mm. The inner edge of the transition zone starts from the edge of the optical zone and extend to the base of the cornea at 8 mm to 11 mm or all the way to the limbus.

Wavefront Correction by Controlling a Bulk Profile of the Cured Material

A method of correcting wavefront aberration of the eye is also provided. In one embodiment, a planar layer of stromal tissue in the range of 5 to 150 microns in thickness, e.g., multiples of 5 microns, is vaporized using a femtosecond laser. After the material is injected, one can first apply wavefront error correction in the material layer. Then, one can perform applanation to correct the sphere and astigmatism (the low order errors) of the eye.

The wavefront errors of the eye are first captured using a aberrometer. There are commercial units available in the market. Advanced Medical Optics, Alcon Labs, Bausch and Lomb, Ophthonix, and Wavefront Sciences are among the commercial aberrometer manufacturers. General principles of correcting wavefront errors using polymer curing has been described in US application 20030143391A1, which is incorporated by reference. The aberrations of the eye are compensated by the optical path difference effected by the thickness profile of the cured material. For example, if the wavefront aberrometer image shows a deficiency of optical path length at one location of the cornea, the thicker cured material in the pocket at the same location increases the optical path length and hence compensates the aberration.

In the exemplary configurations of FIGS. 2(c) and 2(d), the central optical zone region 50 is filled with injected material. In this region, wavefront correction is preferably applied. From a wavefront aberrometer measurement, aberrations of the eye are represented as a two dimensional wavefront map, showing an optical path differences (OPD), from an ideal eye. This OPD map is then used to generate a material "thickness" map in the material layer that would cancel the ocular aberrations. The cured thickness is a function of the dosage of curing light at the material. The more curing light dosage that is applied, the thicker the cured layer will be. The thicker the cured material, the longer the optical path length is. One uses the OPD in the material layer to cancel the OPD of the eye.

A number of parameters are then input to a computer, including wavefront measurement data, absorption characteristics of the absorbing agent and absorption characteristics of the photo-activator in the injected material, and the curing light intensity level. The output from the computer is a printed mask, which is a two dimensional map of gray scale that controls degrees of attenuation of the curing light. The region of the mask that has low gray scale and/or less blocking of the curing light will cause a thicker material layer to build in the injected material layer than a region with higher gray scale where less curing light is transmitted.

For the actual curing device, an optical relay is put in place between the mask and the patient's eye. A curing light source illuminates the mask. Here we use a broad area source with substantially uniform intensity to illuminate the mask. The light typically includes optical bands UV-A, and UV-B. Relay optics form an image of the mask onto a material layer of the eye. An automatic timer, or a computer-controlled shutter, may turn the light source on and/or off.

This material layer building process may be accomplished without the use of a tightly focused laser beam (see, e.g., US patent application 20030143391A1, hereby incorporated by reference), where a material layer is built by scanning a tightly focused spot and the curing substantially occurs at the beam waist of the focus. The present method may be performed without a scanning device and/or expensive optics for tight focusing. The coherent property requirement of the laser beam to generate a tightly focused beam waist is advantageously relaxed. This method and/or one or more methods described in the US application 20030143391A1 can also be used to create a wavefront correction profile in the injected material.

Another feature is that, using the method of adding a bleachable absorbing agent as described earlier, a wavefront correction profile may be built using a thickness profile of cured material in the pocket. This is distinct from other methods such as that proposed by Calhoun Vision, in U.S. Pat. No. 6,450,642, to cause the polymer network to swell and cause an overall shape change, or methods by Ophthonix in U.S. Pat. No. 6,813,082, wherein the OPD is achieved by a spatial variation of the overall index of refraction in the material medium. Both U.S. Pat. Nos. 6,450,642 and 6,813,082 are incorporated by reference. Either of the Calhoun or Ophthonix methods can also be used to effect the OPD to compensate refractive errors of the eye in alternative embodiments.

Multiple-Pocket Procedures

In another embodiment, wavefront correction and a shape change of the eye by applanation can be accomplished in two steps resulting from polymer material injected into two separate corneal pockets. The two pockets are to be made at different depths in the stromal layer of the eye. For example, the wavefront correction pocket may be at a depth of 150 micron, and the shape-change pocket at 300 microns, or vice versa. The depths may vary from this example. The wavefront pocket can be smaller in diameter, e.g., when it is desired to correct wavefront errors near a central portion of the eye. Alternatively, if one prefers to correct refractive errors or create a multi-focal cornea, an annular shaped pocket can be made. The applanator may be machined into a multi-focal curvature. The central cornea is preferably not corrected by this procedure. A flatter curvature is applanated to the annular region to achieve a myopia correction for near distance viewing and reading. Alternatively, the annular region may be applanated to provide a steeper curvature for a hyperopic correction in that region. Wavefront aberration correction can also be applied to either pocket. For keratoconus eyes, shape-change pocket might not be at the center of the pupil. The wavefront correction pocket might be at the center of the pupil. The pocket location and size may vary with the conditions of the refractive errors or the cone.

Keratoconus Ablation

Without the strengthening of the cornea with the injected material layer, performing a LASIK or PRK to remove cornea tissue to reshape the cone is not advisable. However, after cornea strengthening in accordance with a preferred embodiment, one can perform LASIK/LASEK, or PRK. The applanation procedure can be used to correct over- or under-correction, or de-centered ablation from a LASIK. The LASIK ablation procedure can also be used to fine-tune an imperfection after the applanation procedure.

Additive Procedures—Combining with Lasik to Treat High Myopia and High Hyperopia In the case of high myopia or high hyperopia, a surgeon may typically choose to either not treat with LASIK, LASEK or PRK, or make a compromised ablation with a smaller optical zone diameter. The last option can lead to night glare, halos and/or other visual symptoms. High myopia ablation of LASIK increases the chances of estasia. With a technique in accordance with a preferred embodiment, an added material layer physically enhances the strength of the cornea. Another embodiment would combine a technique in accordance with a preferred embodiment with LASIK to extend the range of refractive correction. As long as the flap is made above the material layer, the remaining tissue thickness can be thin. It is now safe to ablate deeper into the stroma with less concern for estasia. An advantage of extending the correction range of tissue ablation without risking safe margin is thereby achieved.

Polymer Fluid-Two-Component Polymer Systems

One advantage of the injected material is to have polymer systems that have both photo- and thermal reactivity. In one embodiment, shape change and the wavefront correction procedures are first performed with an applanator. Then, thermal energy is used to cure the remaining unused material in the pocket. One advantage of this method is to fix the material so that it does not diffuse into the blood system. This method may enable relaxation of a material requirement so that it is systematically safe and biocompatible with the cornea. In one embodiment, a polymer mixture is chosen that would cure near or above body temperature. The material is kept at low temperature before applying to the eye. After it is injected into the pocket, the material will have for example, up to one hour before it is polymerized into a highly viscous gel or solid form by the thermal process. The refractive change and wavefront correction is to be performed prior to the material being fixed. Alternatively, the material may have a higher curing temperature of 45 degrees Celsius or higher. An additive may be included with the material such that it will absorb a selected wavelength slightly different from the curing light, or absorb electric or magnetic energy. Thereby, one can first cure the material with an applanator to achieve shape and wavefront changes, and then thermally fix the remaining material with a second light source, and/or an electric or a magnetic radiation source.

The present invention is not limited to the embodiments described above herein, which may be amended or modified without departing from the scope of the present invention, which is as set forth in the appended claims and structural and functional equivalents thereof.

In methods that may be performed according to preferred embodiments herein and that may have been described above and/or claimed below, the operations have been described in selected typographical sequences. However, the sequences have been selected and so ordered for typographical convenience and are not intended to imply any particular order for performing the operations.

In addition, all references cited above and below herein, in addition to the background and summary of the invention sections, are hereby incorporated by reference into the detailed description of the preferred embodiments as disclosing alternative embodiments and components. The following are incorporated by reference: 5,984,916, 6,210,401, 5,549,632, as well as 6,976,641, 6,934,088, 6,836,371, 6,761,454, 6,706,036, 6,325,792 and 5,825,562.

What is claimed is:

1. A method of inducing a shape change in a cornea for treating a keratoconus condition, or correcting a refractive error or a high order aberration, or other optical eye treatment, or combinations thereof, comprising:
   (a) generating a beam of laser pulses;
   (b) focusing said beam of pulses to a stromal layer of the patient's eye;
   (c) directing said beam of pulses for ablating an intrastromal pocket within the patient's eye;
   (d) further focusing and directing the beam of pulses to cut an injection port between the intrastromal pocket and a cornea surface of the eye;
   (e) flowing a polymerizable fluid into the intrastromal pocket through the injection port; and (f) curing the fluid to form a polymeric insert, and thereby inducing a cornea shape change, and (g) wherein the curing comprises photoreactive curing with curing light.

2. The method of claim 1, further comprising selecting a pocket location near a cornea center.

3. The method of claim 1, further comprising selecting a pocket location offset from a cornea center toward a cone.

4. The method of claim 1, wherein said generating comprises selecting a femtosecond surgical laser.

5. The method of claim 1, wherein said directing comprises generating a cut pattern including multiple linear cuts.

6. The method of claim 1, further comprising applying an applanator to a cornea surface for conforming the eye according to an applanator surface curvature.

7. The method of claim 6, wherein the conforming comprises providing a transition zone of gradual radius of curvature change from an optical zone to an outer zone.

8. The method of claim 1, wherein the curing further comprises thermal curing.

9. The method of claim 1, wherein the polymeric insert comprises approximately 5-150 microns in thickness.

10. The method of claim 1, wherein the polymeric insert comprises approximately 10-75 microns in thickness.

11. The method of claim 1, further comprising further focusing and directing the beam of pulses to cut one or more further injection ports between the intrastromal pocket and the cornea surface of the eye, and flowing polymerizable fluid into the intrastromal pocket through the one or more further injection port.

12. The method of claim 1, further comprising further focusing and directing the beam of pulses to a different location of the stromal layer of the patient's eye for ablating a second intrastromal pocket within the patient's eye; and flowing polymerizable fluid into the second intrastromal pocket through the same or a different injection port.

13. The method of claim 1, further comprising sealing the injection port.

14. The method of claim 1, further comprising pre-mixing the polymerizable fluid with one or more non-toxic light absorbing agents.

15. The method of claim 1, wherein the polymeric insert has regions of different selected thicknesses for correcting wavefront aberration.

16. A method of inducing a shape change in a cornea for treating a keratoconus condition, or correcting a refractive error or a high order aberration, or other optical eye treatment, or combinations thereof, comprising:

(a) generating a beam of laser pulses;

(b) focusing said beam of pulses to a stromal layer of the patient's eye;

(c) directing said beam of pulses for ablating an intrastromal pocket within the patient's eye;

(d) further focusing and directing the beam of pulses to cut an injection port between the intrastromal pocket and a cornea surface of the eye;

(e) flowing a polymerizable fluid into the intrastromal pocket through the injection port; and (f) curing the fluid to form a polymeric insert, and thereby inducing a cornea shape change, wherein the curing comprises applying UV light through a mask to provide a pattern for the polymeric insert.

17. A method of inducing a shape change in a cornea for treating a keratoconus condition, or correcting a refractive error or a high order aberration, or other optical eye treatment, or combinations thereof, comprising:

(a) generating a beam of laser pulses;

(b) focusing said beam of pulses to a stromal layer of the patient's eye;

(c) directing said beam of pulses for ablating an intrastromal pocket within the patient's eye;

(d) further focusing and directing the beam of pulses to cut an injection port between the intrastromal pocket and a cornea surface of the eye;

(e) flowing a polymerizable fluid into the intrastromal pocket through the injection port;

(f) curing the fluid to form a polymeric insert, and thereby inducing a cornea shape change, and (g) adding a bleachable absorbing agent to the polymerizable fluid.

18. A method of changing the shape of a cornea, comprising:

(a) generating a substantially closed pocket in a stroma of an eye, and at least one opening connecting a cornea surface to the pocket, wherein a size of the opening is substantially smaller than an area of the pocket;

(b) injecting a polymerizable fluid in the pocket through the opening;

(c) conforming an anterior surface of the cornea to a shaped surface of an applanator; and (d) applying radiation energy to cure the injected material to form a rigid layer, and to maintain a permanent shape change of the cornea, and (e) reversing the method comprising removing the material of the rigid layer using a scissor and cutting the material through a small opening at the cornea.

19. A method of changing the shape of a cornea, comprising:

(a) generating a substantially closed pocket in a stroma of an eye, and at least one opening connecting a cornea surface to the pocket, wherein a size of the opening is substantially smaller than an area of the pocket;

(b) injecting a polymerizable fluid in the pocket through the opening;

(c) conforming an anterior surface of the cornea to a shaped surface of an applanator; and (d) applying radiation energy to cure the injected material to form a rigid layer, and to maintain a permanent shape change of the cornea, and (e) wherein the applying radiation energy comprises curing the polymerizable fluid to form a polymeric insert, and thereby inducing said permanent shape change, and (f) wherein the curing comprises photoreactive curing with curing light.

20. The method of claim 19, wherein the shaped surface of the applanator conforms the cornea and decreases a diopter value or radius of curvature, or both, of the cornea to correct a myopia condition of the eye.

21. The method of claim 19, wherein the shaped surface of the applanator conforms the cornea and increases a diopter value of the cornea to correct a hyperopia condition of the eye.

22. The method of claim 19, wherein the shaped surface of the applanator conforms the cornea and decreases an asymmetry of the cornea to correct astigmatism of the cornea.

23. The method of claim 19, wherein the shaped surface of the applanator conforms the cornea and corrects a wavefront aberration of the eye.

24. The method of claim 19, wherein the shaped surface of the applanator conforms the cornea to reduce a bulge of a cone to correct a keratoconus condition of the eye.

25. The method of claim 19, wherein the rigid layer has an optical zone that corrects a refractive error of the eye, and a transition zone that changes a radius of curvature from that at an inner edge of the transition zone to that of a base cornea curvature at an outer edge of the transition zone.

26. The method of claim 19, further comprising producing a cured pattern of injected fluid to form a plurality of openings in the form of grids across the rigid layer.

27. The method of claim 19, further comprising curing the polymer fluid to provide an optical path difference (OPD) map for substantially canceling a wavefront aberration of the eye.

28. The method claim of 27, wherein the OPD map is substantially built by a thickness profile of cured material, a change of index of refraction in injected polymer, or a volume expansion of cured material in the rigid layer.

29. A method of changing the shape of a cornea, comprising:
(a) generating a substantially closed pocket in a stroma of an eye, and at least one opening connecting a cornea surface to the pocket, wherein a size of the opening is substantially smaller than an area of the pocket;
(b) injecting a polymerizable fluid in the pocket through the opening;
(c) conforming an anterior surface of the cornea to a shaped surface of an applanator; and
(d) applying radiation energy to cure the injected material to form a rigid layer, and to maintain a permanent shape change of the cornea, and
(e) wherein the polymerizable fluid comprises of a light activated component and a thermally activated component, such that the light activated component provides the rigid layer, and the thermally activated component increases a viscosity, or turns into solid, or a combination thereof, of remaining uncured material.

30. A method of enhancing a mechanical strength of a cornea, comprising:
(a) generating a pocket in a stroma of an eye having an opening to a cornea surface substantially smaller than a size of the pocket;
(b) injecting a polymerizable fluid into the pocket through the opening; and
(c) applying radiation energy to the injected fluid to form a rigid layer, and
(d) wherein the applying radiation energy comprises curing the polymerizable fluid to form a polymeric insert, and thereby inducing a cornea shape change, and
(e) wherein the curing comprises photoreactive curing with curing light.

31. The method of claim 30, further comprising applying thermal curing to the rigid layer or injected fluid or both.

32. A method of changing a shape of a cornea, comprising:
(a) generating multiple excision channels in the stromal layer of a cornea and at least one opening connecting a cornea surface to the channels, wherein a size of each opening is substantially smaller than an area occupied by the channels;
(b) injecting a polymerizable fluid to fill the channels through the at least one opening;
(c) conforming an anterior surface of the cornea to a shaped surface of an applanator; and
(d) applying radiation energy to the fluid to form a rigid layer for maintaining a permanent shape change of the cornea, and
(e) wherein the applying radiation energy comprises curing the polymerizable fluid to form a polymeric insert, and thereby inducing a cornea shape change, and
(f) wherein the curing comprises photoreactive curing with curing light.

33. The method of claim 32, wherein the channels comprise a grid-like configuration or a spoke-like configuration, or a combination thereof.

34. The method of claim 32, wherein the channels comprise multiple spokes.

35. The method of claim 34, wherein said channels further comprise one or more rings approximately normal to the spokes.

36. The method of claim 34, wherein the spokes terminate at a predetermined radius from a center, thereby leaving a central portion of predetermined radius devoid of said channels.

37. The method of claim 36, wherein said channels further comprise one or more rings approximately normal to the spokes.

* * * * *